United States Patent [19]

Kuo

[11] Patent Number: 5,416,112
[45] Date of Patent: May 16, 1995

[54] N-PHENYL-2-CYANO-3-HYDROXY-PROPENAMIDES

[75] Inventor: Elizabeth A. Kuo, Swindon, United Kingdom

[73] Assignee: Roussel Uclaf, France

[21] Appl. No.: 254,162

[22] Filed: Jun. 6, 1994

[30] Foreign Application Priority Data

Jun. 29, 1993 [GB] United Kingdom ............... 9313365

[51] Int. Cl.⁶ ............... A61K 31/275; C07C 255/23
[52] U.S. Cl. ................................... 514/521; 514/466;
514/522; 549/434; 549/436; 549/438; 549/439;
549/441; 558/392
[58] Field of Search ............... 558/392; 514/521, 522,
514/466; 549/434

[56] References Cited

U.S. PATENT DOCUMENTS

| | | | |
|---|---|---|---|
| 5,240,960 | 8/1993 | Hambleton et al. ............... | 558/392 |
| 5,308,865 | 5/1994 | Bartlett et al. ............... | 558/392 |
| 5,312,830 | 5/1994 | Kuo ............................... | 558/392 |

FOREIGN PATENT DOCUMENTS

| | | |
|---|---|---|
| 0551230 | 7/1993 | France . |
| 2524929 | 1/1980 | Germany . |
| PCT/EP900-1800 | 10/1990 | WIPO . |

OTHER PUBLICATIONS

Axton, et. al., Chem. Soc. Perkin. Trans. 1(1992), pp. 2203-2213.

*Primary Examiner*—Joseph Paul Brust
*Attorney, Agent, or Firm*—Bierman & Muserlian

[57] ABSTRACT

A compound selected from the group consisting of a compound of the formula

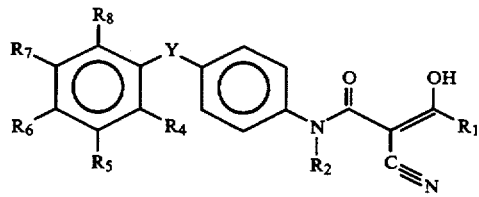

wherein $R_1$ is selected from the group consisting of alkyl of 1 to 6 carbon atoms, cycloalkyl of 3 to 6 carbon atoms and alkenyl and alkynyl of 2 to 6 carbon atoms, $R_2$ is hydrogen or alkyl of 1 to 3 carbon atoms, Y is selected from the group consisting of

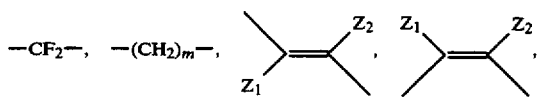

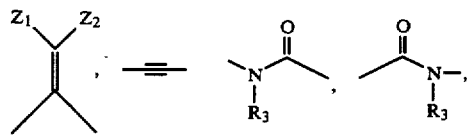

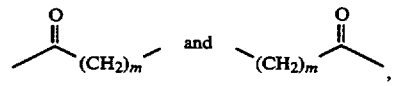

$Z_1$ and $Z_2$ are individually selected from the group consisting of hydrogen, halogen, $-NO_2$, $-CN$ and alkyl of 1 to 3 carbon atoms, $R_3$ is hydrogen or alkyl of 1 to 3 carbon atoms, m is an integer from 0 to 6, $R_4$, $R_5$, $R_6$, $R_7$ and $R_8$ are individually selected from the group consisting of hydrogen, halogen, $-CN$, $-NO_2$, alkyl, alkylthio and alkoxy of 1 to 6 carbon atoms, cycloalkyl of 3 to 6 carbon atoms, $-COR_{10}$, $-(CH_2)_n-CX_3$, $-O-(CH_2)_n-CX_3$ and $-S-(CH_2)_n-CX_3$, $R_{10}$ is selected from the group consisting of hydrogen, alkyl of 1 to 6 carbon atoms and cycloalkyl of 3 to 6 carbon atoms, n is an integer from 0 to 3, X is halogen or $R_6$ and $R_7$ together form $-O-CH_2-O-$ and their non-toxic, pharmaceutically acceptable salts with a base having anti-inflammatory and immunomodulatory activity.

14 Claims, No Drawings

N-PHENYL-2-CYANO-3-HYDROXY-PROPENA-MIDES

OBJECTS OF THE INVENTION

It is an object of the invention to provide the novel propenamides of formula I and their non-toxic, pharmaceutically acceptable salts and a process and intermediates for their preparation.

It is another object of the invention to provide novel antiinflammatory compositions and a novel method of treating inflammation in warm-blooded animals.

These and other objects and advantages of the invention will become obvious from the following detailed description.

THE INVENTION

The novel compounds of the invention are selected from the group consisting of a compound of the formula

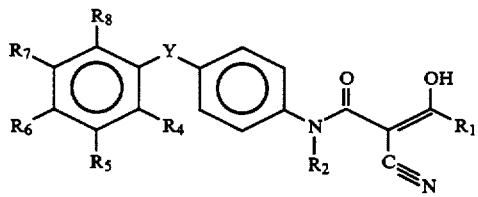

I wherein $R_1$ is selected from the group consisting of alkyl of 1 to 6 carbon atoms, cycloalkyl of 3 to 6 carbon atoms and alkenyl and alkynyl of 2 to 6 carbon atoms, $R_2$ is hydrogen or alkyl of 1 to 3 carbon atoms, Y is selected from the group consisting of

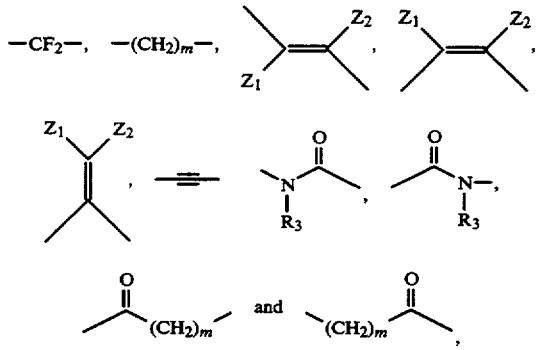

$Z_1$ and $Z_2$ are individually selected from the group consisting of hydrogen, halogen, —$NO_2$, —CN and alkyl of 1 to 3 carbon atoms, $R_3$ is hydrogen or alkyl of 1 to 3 carbon atoms, m is an integer from 0 to 6, $R_4$, $R_5$, $R_6$, $R_7$ and $R_8$ are individually selected from the group consisting of hydrogen, halogen, —CN, —$NO_2$, alkyl, alkylthio and alkoxy of 1 to 6 carbon atoms, cycloalkyl of 3 to 6 carbon atoms, —$COR_{10}$, —$(CH_2)_n$—$CX_3$, —O—$(CH_2)_n$—$CX_3$, and —S—$(CH_2)_n$—$CH_3$, $R_{10}$ is selected from the group consisting of hydrogen, alkyl of 1 to 6 carbon atoms and cycloalkyl of 3 to 6 carbon atoms, n is an integer from 0 to 3, X is halogen or $R_6$ and $R_7$ together form —O——$CH_2$—O— and their non-toxic, pharmaceutically acceptable salts with a base. The compounds may be in all tautomeric forms.

Examples of alkyl of 1 to 3 carbon atoms are methyl, ethyl, propyl and isopropyl and alkyl of 1 to 6 carbon atoms are methyl, ethyl, propyl, isopropyl and linear or branched butyl, pentyl or hexyl. Examples of cycloalkyl are cyclopropyl, cyclobutyl, cyclopentyl and cyclohexyl.

Examples of alkoxy of 1 to 6 carbon atoms are methoxy, ethoxy, propoxy, isopropoxy and linear or branched, butoxy, pentyloxy and hexyloxy and alkylthio of 1 to 6 carbon atoms are methylthio, ethylthio, propylthio, isopropylthio and branched or linear butylthio, pentylthio and hexylthio. Examples of halogen are fluorine, chlorine, bromine and iodine.

Examples of alkenyl of 2 to 6 carbon atoms are

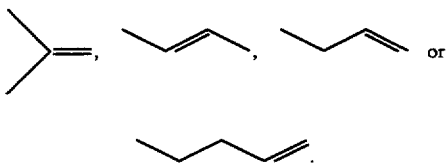

and of alkynyl of 2 to 6 carbon atoms are

Examples of —$(CH_2)_n$—$CX_3$, —O—$(CH_2)_n$—$CX_3$ and —S—$(CH_2)_n$—$CX_3$ are —$CF_3$, —$(CH_2)$—$CF_3$, —$(CH_2)_2$—$CF_3$, —$(CH_2)_3$—$CF_3$, —O—$CF_3$, —O—$(CH_2)$—$CF_3$, —O—$(CH_2)_2$—$CF_3$, —O—$(CH_2)_3$—$CF_3$, —S—$CF_3$, —S—$(CH_2)$—$CF_3$, —S—$(CH_2)_2$—$CF_3$, —S—$(CH_2)_3$—$CF_3$.

The group of the formula:

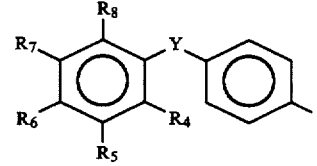

includes, for example, 4-(4'-chlorobenzoyl)-phenyl-, 4-[N-(4-chloro-phenyl)-N-methyl-aminocarbonyl]-phenyl-, 4-(4'-chlorophenyl-E-ethenyl)-phenyl-, 4-(4'-chlorophenyl-ethynyl)-phenyl-, 4-(4'-chlorophenyl-Z-ethenyl)-phenyl-, 4-(4'-fluorophenyl-E-ethenyl)-phenyl-, 4-(4'-fluorophenyl-ethynyl)-phenyl]-, 4-(phenethyl)-phenyl-, 4-biphenylyl- and 4-(4'-fluorophenyl)-phenyl-.

Examples of the salts of the compounds of formula I are non-toxic, pharmaceutically acceptable bases such as sodium, potassium, calcium, magnesium and ammonium salts and organic bases such as methylamine, propylamine, trimethylamine, diethylamine, triethylamine, N,N-dimethylethanolamine, tris(hydroxymethyl)-aminoethane, ethanolamine, pyridine, picoline, dicyclohexylamine, morpholine, benzylamine, procaine, lysine, arginine, histidine and N-methylglucamine.

Preferred compounds are those wherein $R_1$ is cyclopropyl or

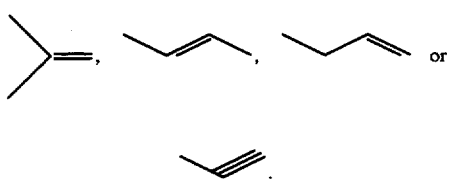

those wherein $R_2$ is hydrogen or methyl and those wherein $R_1$ is cyclopropyl; $R_2$ is hydrogen or methyl; Y is —$(CH_2)_m$— in which m is 0, 1 or 2 or

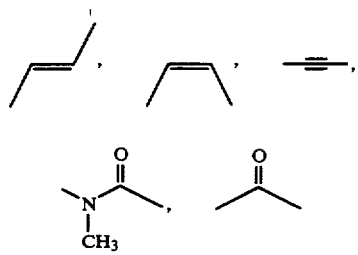

and either $R_4$, $R_5$, $R_6$, $R_7$ and R are individually selected from the group consisting of hydrogen, chlorine, fluorine or bromine, cyano, nitro, methyl, cyclopropyl, methoxy, methylthio, —CO—$R_{10}$ in which $R_{10}$ is hydrogen, methyl or cylcopropyl and —$(CH_2)_n$—$CF_3$, —O—$(CH_2)_n$—$CF_3$ or —S—$(CH_2)_n$—$CF_3$ in which n is 0, 1, 2 or 3; or $R_6$ and $R_7$ together are —O—$CH_2$—O—.

More particularly preferred compounds are those wherein R1 is cyclopropyl; $R_2$ is hydrogen or methyl; Y is —$(CH_2)_m$— in which m is 0, 1 or 2 or

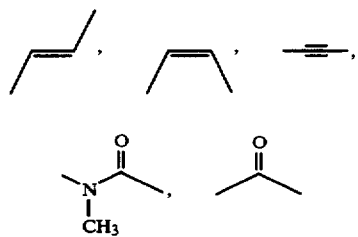

and $R_4$, $R_5$, $R_6$, $R_7$ and $R_8$ are individually selected from the group consisting of hydrogen, chlorine, bromine, fluorine, methyl, nitro and trifluoromethyl.

Especially preferred compounds of the invention are N-[4-4'-chlorophenyl-E-ethenyl)-phenyl]-2-cyano-3-cyclopropyl-3-hydroxy-prop-2-enamide; N-[4-(4'-fluorophenyl-E-ethenyl)-phenyl]-2-cyano-3-cyclopropyl-3-hydroxy-prop-2-enamide; N-(4-biphenyl-2-cyano-3-cyclopropyl-3-hydroxy-prop-2-enamide; N-[4-(4'-fluorophenyl)-phenyl]-2-cyano-3-cyclopropyl-3-hydroxy-prop-2 -enamide and base addition salts thereof.

The process for the preparation of the compounds of formula I comprises reacting a compound of the formula

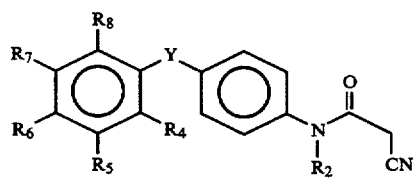

wherein $R_2$, Y, $R_4$, $R_5$, $R_6$, $R_7$ and $R_8$ are as defined above with sodium hydride optionally in the presence of a catalyst and reacting the resulting product with a compound of the formula

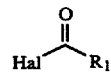

wherein Hal is halogen and $R_1$ is as defined above; or reacting a compound of formula II with sodium hydride optionally in the presence of a catalyst and reacting the resulting product with a compound of the formula

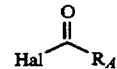

wherein Hal is halogen and $R_A$ is $R_1$ as defined above additionally carrying a protecting group to obtain a compound of the formula

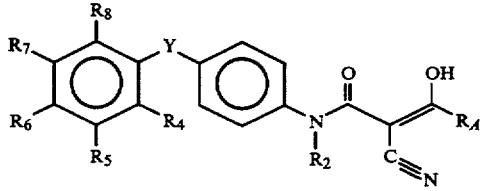

wherein $R_A$, $R_2$, Y, $R_4$, $R_5$, $R_6$, $R_7$ and $R_8$ are as defined above and subsequently cleaving the protecting group to obtain the corresponding compound of formula $I_A$ in which $R_A$ is $R_1$ as defined above.

In the case of any of the processes above, if desired, the compound of formula I obtained may subsequently be converted into a base addition salt thereof by conventional methods.

The reaction between the compound of formula II and sodium hydride is preferably effected in the presence of an anhydrous organic solvent such as tetrahydrofuran or dichloromethane and optionally in the presence of a catalyst capable of solvating the sodium hydride such as imidazole.

The reaction between the product of the reaction of the compound of formula II and sodium hydride and the compound of formula III or $III_A$ is preferably effected in the presence of imidazole and in an anhydrous organic solvent such as tetrahydrofuran or dichloromethane at ambient or low temperature.

The compound of formula III or $III_A$ is preferably an acid chloride or acid fluoride. As an example of the compound of formula III is propynoyl fluoride which can be prepared by reaction of propiolic acid with benzoyl fluoride and distilled into the subsequent reaction mixture.

Where $R_A$ is $R_1$ additionally carrying a protecting group, this protecting group may be an arylseleno, preferably a phenylseleno group. The deprotection of such protecting group may be carried out by oxidation using a peroxide such as hydrogen peroxide, either in the absence of a solvent or in the presence of a mixture of organic solvents such as methanol/dichloromethane.

The compounds of formula II may be prepared by reacting a compound of the formula

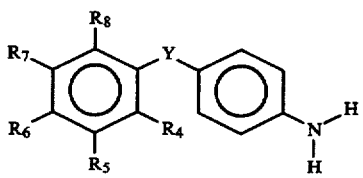

in which Y, R$_4$, R$_5$, R$_6$, R$_7$ and R$_8$ are as defined above with cyanoacetic acid preferably in the presence of dicyclocarbodiimide or phosphorus pentachloride and in the presence of an anhydrous organic solvent such as tetrahydrofuran or dichloromethane.

The compounds of formula IV which are not already known may be prepared by reduction of the corresponding nitro compounds of the formula

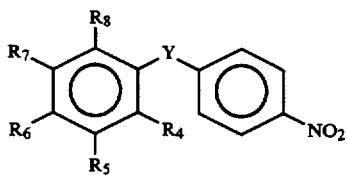

in which Y, R$_4$, R$_5$, R$_6$, R$_7$ and R$_8$ are as defined above.

The compounds of formula I are acidic in character and the base addition salts of the compounds of formula I can advantageously be prepared by reacting, in approximately stoichiometric proportions, an inorganic or organic base with the compound of formula I. The salts can be prepared without intermediate isolation of the corresponding acidic compound.

The anti-inflammatory compositions of the invention are comprised of an anti-inflammatorily effective amount of at least one compound of formula I and its salts with non-toxic, pharmaceutically acceptable bases and an inert pharmaceutical carrier. The compositions may be in the form of tablets, dragees, capsules, granules, suppositories and injectable solutions or suspensions.

Examples of inert pharmaceutical carriers or excipients are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

Because of their remarkable anti-inflammatory activity, they inhibit both the inflammatory response caused by irritant agents, and delayed hypersensitivity reactions by hindering activation of the immune cells by a specific antigen. They are useful in the treatment of rheumatoid arthritis, chronic inflammatory diseases of immune or non-immune origin (e.g. grant- versus- host disease, transplantation reactions, uveitis); and cancer.

The novel method of treating inflammation in warm-blooded animals, including humans, comprises administering to warm-blooded animals an anti-inflammatorily effective amount of at least one compound of formula I and its salts with non-toxic, pharmaceutically acceptable bases. The compounds may be administered orally, rectally or parenterally. The usual effective daily dose is 0.001 to 2.7 mg/kg depending on the condition treated, the specific compound and the method of administeration.

The compounds of formulae II and IV are novel intermediates and are an object of the invention.

In the following examples, there are described several preferred embodiments to illustrate the invention. However, it should be understood that the invention is not intended to be limited to the specific embodiments.

EXAMPLE 1

N-[4-(4'-chlorobenzoyl-phenyl]-2-cyano-3-cyclopropyl-3-hydroxy-prop-2-enamide 6.52 g, 21.8 mmol of N-[4-(4'-chlorobenzoyl-phenyl]-cyanoacetamide were added in several portions over 1 hour to a suspension of 1.97 g of sodium hydride (80% dispersion in oil, 65.5 mmol, 3 equiv) in 100 ml of tetrahydrofuran and after, the mixture was stirred for 1 hour in a solution of 3.42 g (2.97 ml (32.7 1.5 equiv) of cyclopropane carbonyl chloride, in 50 ml was added dropwise. The mixture was stirred for 30 minutes before adding 3.75 ml (65.5 mmol, 3 equiv) of acetic acid cautiously to quench the reaction. After 20 minutes, the reaction mixture was added to a vigorously stirred mixture of 100 ml of 2M HCl in 400 ml of ice-water. The suspension was filtered and the solid washed twice with 50 ml of water then dried in vacuo. The solid was stirred in 150 ml of ether for 30 minutes and filtered. The solid was washed twice with 30 ml of 40–60 petroleum ether and dried in vacuo to obtain 6.84 g (86%) of the desired product. $^1$H nmr $\delta$(CDCl$_3$) 1.12–1.22 (2H, m) 1.28–1.39 (2H, m), 2.11–2.18 (1H, m), 7.03 (2H,s), 7.30–7.55 (9H, m) 15.85 (1H, s).

Preparation of
N-[4-(4'-chlorobenzoyl)-phenyl-cyanoacetamide

STEP 1: 4-chloro-4'-nitro-benzophenone 14.7 g, (110 mmol, 1.1 equiv) of aluminum chloride were added in portions over 40 minutes to a solution of 18.6 g (100 mmol) of 4-nitro-benzoyl chloride in 66 ml (650 mmol, 6.5 equiv) of chlorobenzene. The mixture was stirred at 50° C. for 22 hours, allowed to cool to room temperature, and was added cautiously to 20 ml of concentrated hydrochloric acid in 180 ml of ice water. The mixture was extracted 4 times with 100 ml ether. The combined extracts were washed 3 times with 100 ml of 2% aqueous KOH, 75 ml of brine, then dried over MgSO$_4$, filtered and evaporated to obtain 22.2 g of pale cream powder. Flash column chromatography (2.5–15% EtOAc/40–60 petroleum ether) yielded 19.30 g (74%) of the desired product as a cream solid.

$^1$H nmr (CDCl$_3$) $\delta$7.51 (2H, d), 7.76 (2H, d), 7.92 (2H, d), and 8.36 (2H, d)

STEP 2: 4-amino-4'-chloro-benzophenone

A suspension of 14.4g (54.8 mmol) of 4-chloro-4'-nitrobenzophenone and 66.9 mg, (0.5 mole %) of platinum oxide was stirred under hydrogen in 300 ml of ethanol for 2 hours The mixture was filtered, evaporated and purified by flash column chromatography (2–8% EtOAc/CH$_2$Cl$_2$) to obtain 10.05 g (72%) of the desired product as a yellow solid. $^1$H nmr (CDCl$_3$) $\delta$4.16 (2H, br s), 6.67 (2H, d), 7.43 (2H, d), 7.68 (2H, d), 7.69 (2H, d).

STEP 3: N-[4-(4'-chlorobenzoyl)-phenyl]-cyanoacetamide 6.05 g (71.1 mmol, 1.5 equiv) of cyanoacetic acid were added in portions over 30 minutes to a suspension of 14.8 g, (71.1 mmol, 1.5 equiv) of phosphorus pentachloride in 150 ml of dichloromethane. The solution was refluxed for 30 minutes and a solution of 4-amino-4'-chloro benzophenone (11.0 g, 47.4 mmol) in 50 ml of $CH_2Cl_2$ were added. The mixture was refluxed for 140 minutes, then was allowed to cool to room temperature. 200 ml of saturated aqueous sodium bicarbonate were added with caution. After stirring for 1 hour, the mixture was filtered and the solid was washed twice with 50 ml of water and dried under vacuum to obtain 13.14 g (93%) of the desired product. $^1H$ nmr ($CDCl_3/CD_3OD$) δ3.64 (2H, s), 7.48 (2H, d), 7.70 (2H, d), 7.73 (2H, d), 7.80 (2H,d)

EXAMPLE 2

N-[4-(N-4-chlorophenyl-N'-methyl)-aminocarbonyl)-phenyl]-2-cyano-3-cyclopropyl-3-hydroxy-prop-2-enamide Using the process of example 1, the above mentioned compound was obtained in an 86% yield. $^1H$ nmr ($CDCl_3$) δ1.10–1.23 (2H, m), 1.27–1.36 (2H, m), 2.06–2.18 (1H, m), 3.47 (3H, s), 6.97 (2H,d), 7.21 (2H, d), 7.30 (2H, d), 7.37 (2H, d), 7.58 (1H, s), 15.66 (1H, s).

Preparation of N-[4-[N,-(4-chlorophenyl)-N',-methyl-aminocarbonyl)phenyl]-cyanoacetamide.

STEP 1: N-(4-chloropehnyl)-N-methyl-4-nitrobenzamide.

A solution of 6.53 g (46.1 mmol) of N-methyl-4-chloroaniline in 50 ml of chloroform was added dropwise over 80 minutes to 8.55 g (46.1 mmol) in 150 ml of 4-nitrobenzoyl-chloride chloroform. 100 ml of saturated aqueous sodium bicarbonate were added after 20 minutes and the layers were separated. The organic layer was washed with 100 ml of saturated $NaHCO_3$, 100 ml of water and 50 ml of brine, then dried over $MgSO_4$, filtered and evaporated to obtain crystals. Flash column chromatography (0–10% $EtOAc/CH_2C_2$ eluent) yielded 8.07 g (60%) of the desired product. $^1H$ nmr ($CDCl_3$) δ6 3.50 (3H, s), 6.98 (2H, d), 7.24 (2H, d), 7.45 (2H, d), 8.08 (2H,d)

STEP 2: 4-amino-N-(4-chlorophenyl)-N-methylbenzamide

A solution of 4 ml (ca 40 mmol) of concentrated hydrochloric acid in 50 ml of ethanol and 50 ml of water was added dropwise over 2 hours to a refluxing suspension of 6.34 g 114 mmol, 3 equiv) of iron filings and 11.0 g (37.8 mmol) of N-(4-chlorophenyl)-N-methyl-4-nitrobenzamide in 200 ml of ethanol and 200 ml of water. The mixture was refluxed for 1 hour and allowed to cool to room temperature and then adjusted to a pH of 11 with 10% aqueous sodium hydroxide. The suspension was filtered and the residue washed 3 times with 200 ml of hot ethyl acetate. The solution was evaporated to remove the organics and the aqueous liquid was extracted 3 times with 200 ml of EtOAc. The combined organics were washed twice with 250 ml of water and 100 ml of brine, then dried over $MgSO_4$, filtered and evaporated to obtain 10.4 g of the desired product as an orange solid.

Flash column chromatography (10–40% $EtOAc/CH_2Cl_2$ eluent) yielded 8.53 g (87%) of the desired product as a cream solid. $^1H$ nmr ($CDCl_3$) δ6 3.44 (3H, s), 3.81 (2H, br s), 6.44 (2H, d), 6.98 (2H, d), 7.13 (2H, d) and 7.21 (2H, d)

STEP 3: N-[4-(N'(4-chlorophenyl)-N'-methyl-aminocarbonyl)phenyl]-cyanoacetamide

Using the process of Step 3 of the preparation of Example 1, the above mentioned compound was obtained in 96% yield. $^1H$ nmr ($CDCl_3/CD_3OD$) δ3.46 (3H, s) , 3.53 (2H, s), 6.99 (2H, d), 7.22 (2H, d), 7.25 (2H,d) and 7.39 (2H, d)

EXAMPLE 3

N-[4-(4'-chlorophenyl-E-ethenyl)-phenyl]-2-cyano-3-cyclopropyl-3-hydroxy-prop-2-enamide Using the process of Example 1, the above mentioned compound was obtained in a 56% yield. δ($CDCl_3$) 1.12–1.22 (2H, m), 1.28–1.37 (2H, m), 2.11–2.18 (1H, m) 7.03 (2H, s), 7.30–7.55 (9H, m), 15.85 (1H, s)

Preparation of N-[4-(4'-chlorophenyl-E-ethenyl)-phenyl)-cyanoacetamide

STEP 1: E-4-chlorophenyl-4'-nitrophenyl-ethene 2.21 g (96.1 mmol, 1.05 equiv) of sodium were added in lumps over 105 minutes to 100 ml of ethanol. The solution was stirred for 20 minutes following dissolution of sodium and then was added dropwise over 50 minutes to a solution of 25 g, (91.5 mmol) Diethyl 4-nitrobenzyl phosphonate and 12.9 g, (91.5 mmol) of 4-chlorobenzaldehyde in 150 ml of ethanol. The mixture was stirred for 16 hours, then filtered. The yellow solid was washed twice with 50 ml of petroleum ether and dried in vacuo to obtain 15.35 g (65%) of the desired product. $^1H$ nmr ($CDCl_3$) δ7.11 (1H, d), 7.23 (1H, d), 7.37 (2H, d), 7.49 (2H, d), 7.63 (2H,d) and 8.23 (2H, d)

STEP 2: E-4-aminophenyl-4'-chlorophenyl-ethene

Using the process of Step 2 of the preparation of Example 2, the above mentioned compound was obtained in 71% yield. δ6 ($CDCl_3$) 3.8 (2H, br s), 6.68 (2H, d), 6.85 (1H, d), 7.00 (1H, d), 7.25–7.42 (6H, m)

STEP 3: N-[4-(4'-chloropehnyl-E-ethenyl)-phenyl]-cyanoacetamide

Using the process of Step 3 of the preparation of Example 1, the above mentioned compound was obtained in 80% yield. δH ($CDCl_3/CD_3OD$) 3.59 (2H, s), 7.03 (2H, s), 7.33–7.59 (9H, m)

EXAMPLE 4

N-([4-(4'-chlorophenyl-ethynyl]-phenyl)-2-cyano-3-cyclopropyl-3-hydroxy-prop-2-enamide Using the process of Example 1, the above mentioned compound was obtained in 88% yield. δ($CDCl_3$) 1.12–1.20 (2H, m), 1.28–1.38 (2H, m), 2.11–2.19 (1H, m) 7.33 (2H, d), 7.46 (2H, d), 7.51 (4H, s), 7.59 (1H, s), 15.74 (1H, s)

Preparation of N-{[4-(4'chlorophenyl)-ethynyl]-phenyl-cyanoacetamide

STEP 1: 1-[4-(chlorophenyl)]-1,2-dibromo-2-[4'-(nitrophenyl)]-ethane

A solution of 14.17 g (4.57 ml, 88.9 mmol) of bromine in 50 ml of chloroform was added dropwise over 100 minutes to a solution of 15.4 g (59.1 mmol) of E-4-chlorophenyl-4'-nitrophenyl ethene in 700 ml of $CHCl_3$. The suspension was stirred for 22 hours, then evaporated. Twice, 100 ml of dichloromethane were evaporated off the solid to remove any remaining bromine to obtain 23.4 g (95%) of the desired product as a magnolia colored solid. $^1H$ nmr ($CDCl_3/CD_3OD$) δ5.40 (1H, d), 5.48 (1H, d), 7.41 (2H, d), 7.47 (2H, d), 7.69 (2H, d), 8.29 (2H, d).

STEP 2: 4-chlorophenyl-4'-nitrophenyl-ethyne 150 ml of 50% aqueous sodium hydroxide were added dropwise over 75 minutes to a suspension of 68.3 g(201 mmol 3 equiv) of $Bu_4NHSO_4$ and 28.1 g, (67.0 mmol) of 1-[4-(chlorophenyl)]-1,2-dibromo-2-[4'-(nitrophenyl)]ethene in 200 ml of $CH_2Cl_2$ and 200 ml of hexane $C_6H_{14}$. After 30 minutes, 500 ml of water, then 200 ml of $CH_2Cl_2$ were added. The mixture was filtered, the layers separated, and the aqueous fraction was extracted twice with 100 ml of $CH_2Cl_2$. The combined organics were washed 4 times with 250 ml of water, 100 ml of brine and, then was dried over $MgSO_4$, filtered and evaporated to obtain 29.9 g of a dark green solid.

Flash column chromatography (5→100% EtOAc/40–60petroleum ether then →60% acetone/EtOAc) yielded 16.29 g (94%) of the desired product. $^1H$ nmr $\delta(CDCl_3)$ 7.37 (2H, d), 7.50 (2H, d), 7.67 (2H, d), 8.23 (2H, d)

STEP 3: 4-aminophenyl-4'-chlorophenyl-ethyne

Using the process of Step 2 of the preparation of Example 2, the above mentioned compound was obtained in 70% yield. $\delta(CDCl_3)$ 3.84 (2H, br s), 6.64 (2H, d), 7.26–7.44 (6H, m)

STEP 4: N-{[4-(4'-chlorophenyl)ethynyl]-phenyl}-cyanoacetamide

Using the process of Step 3 of the preparation of Example 1, the above mentioned compound was obtained in 93% yield. $\delta H(d^6\text{-DMSO})$ 3.99 (2H, s), 7.51–7.70 (8H, m), 10.56 (1H, s)

EXAMPLE 5

N-[4'-(4-chlorophenyl-Z-ethenyl)-phenyl]-2-cyano-3-cyclopropyl-3-hydroxy-prop-2-enamide Using the process of Example 1, the above mentioned compound was obtained in 84% yield. $\delta H(d_6\text{-DMSO})$ 0.96–1.02 (4H, m), 2.14–2.24 (1H, m) 6.57 (1H, d), 6.66 (1H, d), 7.18 (2H, d), 7.29 (2H, d), 7.38 (2H, d), 7.47 (2H, d), 11.06 (1H, s)

Preparation of N-[4-(4-chlorophenyl-Z-ethenyl)-phenyl]-cyanoacetamide.

STEP 1: Z-4-chlorophenyl-4'-nitrophenyl-ethene

A mixture of 9.0 g (34.9 mmol) of 4-chlorophenyl-4'-nitro-phenyl-ethyne, 900 mg of palladium on calcium car with lead (Linder catalyst) and 902 mg (825 μl, 7.00 mol, 0.2 equiv) of quinoline were stirred under hydrogen in one liter of ethyl acetate until hydrogen uptake ceased. The mixture was filtered and evaporated. 1H nmr indicated a mixture of starting material and product. Thus, the reaction mixture was dissolved in 175 ml of EtOAc, 1 ml of quinoline and 1.5 g of Linder catalyst were added and hydrogenation restarted. After hydrogen uptake had finished, the mixture was filtered, evaporated and purified by flash column chromatography (5–20% EtOAc/40–60 pet ether eluent) to obtain 7.98 g (88%) of the desired product. $^1H$ nmr $(CDCl_3)\delta6.63$ (1H, d), 6.75 (1H, d), 7.12 (2H, d), 7.23 (2H, d), 7.36 (2H, d), 8.09 (2H, d)

STEP 2: Z-4-aminophenyl-4'-chlorophenyl-ethene

Using the process of Step 2 of the preparation of Example 2, the above mentioned compound was obtained in 53% yield. $\delta(CDCl_3)$ 3.69 (2H, br s), 6.35 (1H, d), 6.50 (1H, d), 6.54 (2H, d), 7.04 (2H, d), 7.20 (4H, s)

STEP 3: N-[4-(4'-chlorophenyl-Z-ethenyl)-phenyl]-cyanoacetamide

Using the process of Step 3 of the preparation of Example 1, the above mentioned compound was obtained in 86% yield. $\delta H(d_6\text{-DMSO})$ 3.94 (2H, s), 6.59 (1H, d), 6.68 (1H, d), 7.23 (2H, d), 7.27 (2H, d), 7.38 (2H, d), 7.50 (2H, d)

EXAMPLE 6

N-[4-(4'-fluorophenyl-E-ethenyl-phenyl]-2-cyano-3-cyclopropyl-3-hydroxy-prop-2-enamide Using the process of Example 1, the above mentioned compound was obtained in 54% yield. $\delta H(d_6\text{-DMSO})$ 1.07–1.13 (4H, m), 2.13–2.28 (1H, m), 7.14–7.44 (4H, m), 7.59–7.75 (6H, m), 10.69 (1H, s)

Preparation of N-[4-(4,-fluorophenyl-E-ethenyl)-phenyl]-cyanoacetamide

STEP 1: E-4-fluorophenyl-4'-nitrophenyl ethene

Using the process of Step 1 of the preparation of Example 3, the above mentioned compound was obtained in 69% yield. $\delta7.01–7.28$ (4H, m), 7.53 (2H, dd), 7.62 (2H, d), 8.23 (2H, d)

STEP 2: E-4-aminophenyl-4'-fluorophenyl ethene

Using the process of Step 2 of the preparation of Example 2, the above mentioned compound was obtained in 81% yield. $\delta(CDCl_3)$ 3.75 (2H, br s), 6.67 (2H, d), 6.90 (2H, m), 7.02 (2H, t), 7.32 (2H, d), 7.43 (2H, dd)

STEP 3: N-[4-(4'-fluorophenyl-E-ethenyl)-phenyl]-cyanoacetamide

Using the process of Step 3 of the preparation of Example 1, the above mentioned compound was obtained in 91% yield. $\delta H(d^6\text{-DMSO})$ 3.97 (2H, s), 7.22 (2H, s), 7.27 (2H, d), 7.61–7.71 (6H, m)

EXAMPLE 7

N-[4-(4'-fluorophenyl-ethynyl)-phenyl]-2-cyano-3-cyclopropyl-3-hydroxyprop-2-enamide Using the process of Example 1, the above mentioned compound was obtained in 84% yield. $\delta H(d^6\text{-DMSO})$ 1.10–1.17 (4H, M), 2.16–2.25 (1H, m), 7.31 (2H, t), 7.46–7.69 (7H, m), 10.74 (1H, s)

Preparation of N{4-[(4'-fluorophenyl)-ethynyl]-phenyl}-cyanoacetamide

STEP 1: 1,2-dibromo-1-(4-fluorophenyl)-2-(4'-nitrophenyl)-ethane

Using the process of Step 1 of the preparation of Example 4, the above mentioned compound was obtained in 93% yield. $\delta H$ 5.42 (2H, s), 7.12 (2H, t), 7.50 (2H, dd), 7.67 (2H, d), 8.28 (2H, d)

STEP 2: 4-fluorophenyl-4'-nitrophenylethyne

Using the process of Step 2 of the preparation of Example 4, the above mentioned compound was obtained in 91% yield. $^1H$ nmr $\delta(CDCl_3)$ 7.09 (2H, t), 7.55 (2H, dd), 7.65 (2H, d), 8.55 (2H, d)

STEP 3: 4-aminophenyl-4'-fluorophenyl ethyne

Using the process of Step 2 of the preparation of Example 2, the above mentioned compound was obtained in 71% yield. $\delta(CDCl_3)$ 3.83 (2H, br s), 6.65 (2H, d), 7.03 (2H, t), 7.34 (2H, d), 7.48 (2H, dd)

STEP 4: N-{4-[(4'-fluorophenyl)ethynyl]-phenyl}-cyanoacetamide

Using the process of Step 3 of the preparation of Example 1, the above mentioned compound was obtained in 93% yield. $\delta H(d^6\text{-DMSO})$ 3.99 (2H, s), 7.31 (2H, t), 7.54–7.68 (6H, m), 10.56 (1H, s)

EXAMPLE 8

N-[4-(phenethyl)-phenyl]-2-cyano-3-cyclopropyl-3-hydroxy-prop-2-enamide

Using the process of Example 1, the above mentioned compound was obtained in 28% yield. $\delta$H(d$^6$-DMSO) 1.15–1.26 (4H, m), 2.18–2.24 (1H, m), 2.90 (4H, s) 7.18–7.36 (7H, m), 7.46 (2H, d), 10.24 (1H, s)

Preparation of N-{4-[2-(phenethyl)-phenyl}-cyanoaoetamide

1: E-4-(nitrophenyl)-2-phenylethene

Using the process of Step 1 of the preparation of Example 3, the above mentioned compound was obtained in 76% yield≈3:1 mixture of trans:cis isomers.

STEP 2: 1-(4-aminophenyl)-2-phenyl ethane

A mixture of 14.7 g (65.4 mmol) of E-4-(nitrophenyl)-2phenylethene and 82 mg (327 $\mu$mol, 5 mole %) of platinum oxide was stirred under hydrogen in 500 ml of ethanol for 19 hours suspension was filtered through celite and evaporated to obtain 14.7 g (<100%) of the desired product as yellow crystals. $\delta$H (CDCl$_3$) 2.76–2.87 (4H, m), 3.53 (2H, br s), 6.61 (2H, d), 6.96 (2H, d), 7.13–7.31 (5H, m)

STEP 3: N-[4-[2-(phenethyl)-phenyl]-cyanoacetamide

Using the process of example 1, the above mentioned compound was obtained in 80% yield. $\delta$H(d$^6$-DMSO) 2.88 (4H, s), 3.91 (2H, s), 7.19–7.36 (7H, m), 7.48 (2H, d), 10.32 (1H, s)

EXAMPLE 9

N-[4-biphenyl -2-cyano-3-cyclopropyl-3-hydroxy-prop-2-enamide

Using the process of Example 1, the above mentioned compound was obtained in 67% yield. $\delta$H (CDCl$_3$) 1.11–1.24 (2H, m), 1.27–1.43 (2H, m), 2.12–2.20 (1H m), 7.26–7.63 (10H, m) 15.89 (1H, s)

Preparation of N-[4-biphenylyl]-cyanoacetamide.

STEP 1: 4-nitrobiphenyl 12.50 g (61.9 mmol) of 1-bromo-4-nitrobenzene were added to 358 mg, (310 $\mu$mol, 0.5 mole %) of tetrakis (triphenyl-phosphine) palladium in 200 ml of dimethoxy-ethane. After stirring for 10 minutes, 11.3 g (92.8 mmol) of phenylboronic acid and 100 ml of ethanol were added. After a further 10 minutes, 263 ml, (526 mmol, 8.5 equiv) of 2M aqueous sodium carbonate were added and the suspension was heated at reflux for 20 minutes, then allowed to cool to room temperature. The mixture was taken into 250 ml of EtOAc and 200 ml of H$_2$. The aqueous layer was extracted with 200 ml of EtOAc and the combined organics were washed twice with 250 ml of water and 100 ml of brine, dried over MgSO$_4$, filtered and evaporated to obtain 15.7 g of the desired product as a solid.

Flash column chromatography (2.5–15% ETOAc/40–60 petroleum ether) yielded 11.8 g (96%) of product as a pale yellow solid. $\delta$H (CDCl$_3$) 7.43–7.55 (3H, m), 7.58–7.65 (2H, m), 7.73 (2H, d), 8.29 (2H, d)

STEP 2: 4-aminobiphenyl

Using the process of Step 2 of the preparation of Example 8, the above mentioned compound was obtained. $^1$H nmr $\delta$(CDCl$_3$) 3.72 (2H, br s), 6.76 (2H, d), 7.25–7.28 (1H, m), 7.35–7.45 (4H, m), 7.51–7.57 (2H, m)

STEP 3: N-[4-biphenylyl]-cyanoacetamide

Using the process of Step 3 of the preparation of Example 1, the above mentioned compound was obtained in 72% yield. $\delta$H (d$^6$-DMSO) 3.99 (2H, s), 7.37–7.54 (3H, m), 7.67–7.73 (6H, m), 10.46 (1H, s)

EXAMPLE 10

N-[4-(4'-fluorophenyl)-phenyl]-2-cyano-3-cyclopropyl-3-hydroxyprop-2-enamide

Using the process of Example 1, the above mentioned compound was obtained in 65% yield. $\delta$H (d$^6$-DMSO) 1.02–1.08 (4H, m), 2.16–2.28 (1H, m), 7.32 (2H, dd), 7.64–7.77 (6H, m) 10.97 (1H, br s)

Preparation of N-[4-(4'-fluorophenyl)-phenyl]-cyanoacetamide

Using the process of Step 3 of the preparation of Example 1, the above mentioned compound was obtained in 91% yield. $\delta$H (d$^6$-DMSO) 3.99 (2H, s), 7.32 (2H, dd), 7.68–7.77 (6H, m), 10.56 (1H, s)

EXAMPLE 11

N-[4, -(4'-chlorophenylmethyl)-phenyl]-2-cyano-3-cyclopropyl-3-hydroxy-prop-2-amide Using the process of Example 1, the above mentioned compound was obtained in 83% yield. $\delta$H (CDCl$_3$) 1.11–1.22 (2H, m), 1.25–1.35 (2H, m), 2.10–2.19 (1H, m), 3.93 (2H, s), 7.00–7.40 (8H, m), 7.47 (1H, s), 15.87 (1H, s)

Preparation of N-[4-(4'-chlorophenylmethyl)-phenyl]-cyanoacetamide

STEP 1: 4-chloro-4'-nitro-benzophenone

Prepared as described in Step 1 for Example 1.

STEP 2: 4-amino-4'-chloro-benzophenone

Prepared as described in Step 2 for Example 1.

STEP 3: 4-(4'-chlorophenylmethyl)-aniline

A suspension of 4.27 g (18.4 mmols) of 4-amino-4' chloro-benzophenone and 8.54 g of zinc amalgam in 80 ml of toluene containing 4 ml of water was heated to reflux. 1 ml of concentrated hydrochloric acid were added over 90 minutes. After 22 hours, the mixture was allowed to cool to room temperature and 100 ml of ethyl acetate and 2×100 ml of water were added. The layers were separated and the aqueous phase was extracted with 50 ml of ethyl acetate. The combined organics were washed twice with 100 ml of water and 50 ml of brine, dried over MgSO$_4$, filtered and evaporated to obtain 3.03 g of orange oil. Flash chromatography (20–35% ethyl acetate/pet ether eluent) yielded the above mentioned product as an orange liquid 915 mg (24.6% yield). $^1$H nmr (CDCl$_3$) $\delta$3.58 (2H, br s), 3.82 (2H, s), 6.62 (2H, d), 6.94 (2H, d), 7.08 (2H, d), 7.22 (2H, d)

STEP 4: N-[4-(4' chlorophenylmethyl)-phenyl]-cyanoacetamide

Using 4-(4'-chlorophenylmethyl)-aniline as starting material and the process of Step 3 of Example 1, the above mentioned product was obtained in 83% yield. 1H nmr (d$^6$-DMSO) $\delta$3.92 (4H, s), 7.23 (2H, d), 7.28 (2H, d), 7.39 (2H, d), 7.50 (2H, d), 10.32 (1H, s)

EXAMPLE 12

N-[4-[2-(4'-chlorophenyl)-ethyl]-phenyl]-2-cyano-3-cyclopropyl-3-hydroxy-prop-2-enamide Using the process of Example 1, the above mentioned compound was obtained.

Spectral date, yields, melting points and analytical data for the Examples are given in Table I.

TABLE I

![structure: ArN(H)-C(=O)-CH=C(OH)-cyclopropyl with CN on the carbon bearing OH]

| Example | Ar | Yield % | mpt °C. | IR cm⁻¹ | ¹H nmr δ | Formula m. wt. | Calc Found % C | H | N | X | |
|---|---|---|---|---|---|---|---|---|---|---|---|
| 1 | 4-(4-chlorobenzoyl)phenyl | 86 | 168-70 | 3285, 2210, 1645, 1570, 1540 | CDCl₃: -1.18-1.26(2H, m), 1.32-1.40(2H, m), 2.13-2.19 (1H, m), 7.48(2H, d), 7.64 (2H, d), 7.70(1H, s), 7.74 (2H, d), 7.83(2H, d), 15.60 (1H, s) | C₂₀H₁₅ClN₂O₃ 366.80 | 65.48 65.30 | 4.12 4.26 | 7.64 7.54 | Cl | 9.67 9.67 |
| 2 | 4-[N-methyl-N-(4-chlorophenyl)carbamoyl]phenyl | 86 | 204-5 | 3250, 2210, 1620, 1585, 1580, 1520, 1485, 1420, 1410, 1375, 1345, 1305, 1295, 1265, 1235, 895, 760 | CDCl₃: -1.10-1.23(2H, m), 1.27-1.36(2H, m), 2.06-2.18 (1H, m), 3.47(3H, s), 6.97 (2H, d), 7.21(2H, d), 7.30 (2H, d), 7.37(2H, d), 7.58 (1H, s), 15.66(1H, s) | C₂₁H₁₈ClN₃O₃ 395.85 | 63.72 63.62 | 4.58 4.94 | 10.62 10.09 | Cl | 8.96 8.62 |
| 3 | 4-[(E)-2-(4-chlorophenyl)ethenyl]phenyl | 56 | 213-7 | 3280, 2215, 1570, 1530, 1510, 1485, 1420, 1350, 1315, 1240, 1085, 895, 830 | CDCl₃: -1.12-1.22(2H, m), 1.28-1.37(2H, m), 2.11-2.18 (1H, m), 7.03(2H, s), 7.30-7.55(9H, m), 15.85(1H, s) | C₂₁H₁₇ClN₂O₂ 364.83 | 69.14 68.94 | 4.70 4.83 | 7.68 7.70 | Cl | 9.72 9.89 |
| 4 | 4-[2-(4-chlorophenyl)ethynyl]phenyl | 88 | 205-7 | 3295, 2220, 1610, 1590, 1540, 1510, 1410, 1350, 1085, 990, 940, 930, 915 | CDCl₃: -1.12-1.20(2H, m), 1.28-1.38(2H, m), 2.11-2.19 (1H, m), 7.33(2H, d), 7.46 (2H, d), 7.51(4H, s), 7.59 (1H, s), 15.74(1H, s) | C₂₁H₁₅ClN₂O₂ 362.82 | 69.52 69.38 | 4.17 4.29 | 7.72 7.68 | Cl | 9.77 9.98 |
| 5 | 4-[(Z)-2-(4-chlorophenyl)ethenyl]phenyl | 84 | 182-3 | 3300, 2230, 1585, 1540, 1495, 1425, 1360, 1330, 1095, 900, 890, 870, 835, 815 | d⁶ DMSO: - 0.96-1.02 (4H, m), 2.14-2.24(1H, m), 6.57 (1H, d), 6.66(1H, d)7.18 (2H, d), 7.29(2H, d), 7.38 (2H, d), 7.47(2H, d), 11.06 (1H, s) | C₂₁H₁₇ClN₂O₂ 364.83 | 69.14 69.07 | 4.70 4.87 | 7.68 7.62 | Cl | 19.72 9.71 |

TABLE I-continued

[Structure: ArN(H)−C(=O)−CH=C(OH)−cyclopropyl with CN on the alkene carbon]

| Example | Ar | Yield % | mpt °C. | IR cm$^{-1}$ | $^1$H nmr δ | Formula m. wt. | Calc / Found % C | H | N | X | |
|---|---|---|---|---|---|---|---|---|---|---|---|
| 6 | 4-CH$_3$-C$_6$H$_4$−CH=CH−C$_6$H$_4$-4-F | 54 | >200 | 3280, 2220, 1605, 1570, 1535, 1505, 1420, 1355, 1230, 1205, 830 | d$^6$ DMSO: - 1.07–1.13 (4H, m), 2.13–2.28(1H, m), 7.14–7.44(4H, m), 7.59–7.75 (6H, m), 10.69(1H, s) | C$_{21}$H$_{17}$FN$_2$O$_2$ 348.36 | 72.40 / 71.86 | 4.92 / 4.98 | 8.04 / 7.89 | F | 5.45 / 5.48 |
| 7 | 4-CH$_3$-C$_6$H$_4$−C≡C−C$_6$H$_4$-4-F | 84 | 213-4 | 3300, 2210, 1600, 1580, 1530, 1515, 1440, 1420, 1345, 1310, 1270, 1240, 1325, 1220, 895, 840 | d$^6$ DMSO: - 1.10–1.17 (4H, m), 2.16–2.25(1H, m), 7.31(2H, t), 7.46–7.69 (7H, m), 10.74(1H, s) | C$_{21}$H$_{15}$FN$_2$O$_2$ 346.35 | 72.82 / 72.55 | 4.37 / 4.61 | 8.09 / 7.86 | F | 5.49 / 5.35 |
| 8 | 4-CH$_3$-C$_6$H$_4$−CH$_2$CH$_2$−C$_6$H$_5$ | 28 | 154-5 | 3300, 2200, 1600, 1570, 1540, 1515, 1410, 1355, 1345, 1310, 1270, 1240, 895, 720, 700 | d$^6$ DMSO: - 1.15–1.26 (4H, m), 2.18–2.24(1H, m), 2.90(4H, s), 7.18–7.36 (7H, m), 7.46(2H, d), 10.24 (1H, s) | C$_{21}$H$_{20}$ClN$_2$O$_2$ 332.39 | 75.88 / 75.71 | 6.07 / 6.22 | 8.43 / 8.45 | | |
| 9 | 4-CH$_3$-C$_6$H$_4$−C$_6$H$_5$ (biphenyl) | 67 | 202-3 | 3320, 2205, 1620, 1580, 1570, 1520, 1480, 1445, 1405, 1345, 1315, 1295, 1275, 1255, 1235, 895, 835, 765 | CDCl$_3$: - 1.11–1.24(2H, m), 1.27–1.43(2H, m), 2.12–2.20 (1H, m), 7.26–7.63(10H, m), 15.89(1H, s) | C$_{19}$H$_{16}$N$_2$O$_2$ | 74.98 / 74.59 | 5.30 / 5.47 | 9.20 / 8.96 | | |

TABLE I-continued
$$\underset{ArN}{\overset{H}{\underset{\|}{C}}}\overset{O}{\underset{\|}{C}}\overset{OH}{\underset{\|}{C}}\overset{\triangle}{\underset{CN}{C}}$$
| Example | Ar | Yield % | mpt °C. | IR cm$^{-1}$ | $^1$H nmr δ | Formula m. wt. | Calc Found % C | H | N | X | |
|---|---|---|---|---|---|---|---|---|---|---|---|
| 10 | 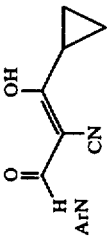 | 65 | 222–3 | 3305, 2205, 1600, 1580, 1530, 1500, 1420, 1345, 1320, 1295, 1210, 1155, 990, 890, 815 | d$^6$ DMSO: - 1.02–1.08 (4H, m), 2.16–2.28(1H, m), 7.32(2H, m), 7.64–7.77 (6H, m), 10.97(1H, s) | C$_{19}$H$_{15}$FN$_2$O$_2$ 322.34 | 70.80 70.52 | 4.69 4.76 | 8.69 8.64 | F | 5.89 5.95 |
| 11 | 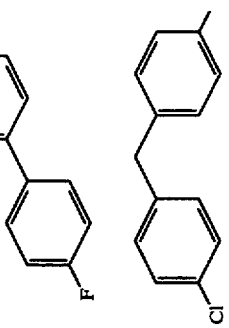 | 83 | 176–7 | 3290, 2215, 1605, 1580, 1540, 1510, 1485, 1420, 1400, 1340, 1315, 1235, 1010, 985, 895, 815, 790 | CDCl$_3$: - 1.11–1.22(2H, m), 1.25–1.35((2H, m), 2.10–2.19(1H, m), 3.93(2H, s), 7.00–7.40(8H, m), 7.47(1H, s), 15.87(1H, s) | C$_{20}$H$_{17}$ClN$_2$O$_2$ | 68.09 68.21 | 4.86 5.10 | 7.94 7.71 | Cl | 10.05 9.88 |

EXAMPLE 13

Tablets containing 20 of the compound of Example 1 or Example 2 and sufficient excipient of lactose, starch, talc, magnesium stearate for one tablet up to 150 mg.

PHARMACOLOGICAL ACTIVITY
Biochemical Test Methods

Test 1: Carrageenan rat paw oedema (PO-R)

One hour after the oral administration of the test compounds or control vehicle to groups of 6 to 12 male rats (CFHB, weight range 160–180 g), 1 mg of carrageenan dissolved in 0.2 ml of saline was injected into the right hind foot pad. Contralateral paws received control saline injections. Paw oedema responses were assessed three hours later.

TEST 2: Delay type hypersensitivity mouse paw oedema (DTH-M)

Groups of 8 to 10 male CD-1 mice with a weight range of 25–30 g were sensitized by the subcutaneous injection of 1mg of methylated bovine serum albumin (MBSA) in 0.2 ml volumes of saline/Freund's complete adjuvant (FCA) emulsion. Negative control groups received injections of saline/FCA emulsion. DTH paw oedema responses were assessed twenty-four hours after the right hind foot pad challenge with 0.1 mg of MBSA in 0.5 ml volumes of saline on day seven after sensitization. Contralateral paws received control saline injections. The test compounds or control vehicles were orally administered daily on days four, five, six and twice on day seven, one hour before and six hours after MSBA challenge.

Test 3: Delayed-type hypersensitivity rat paw oedema (DTH-R)

Groups of 8 to 12 male CFHB, weight range 160–180 g rats were sensitized by the subcutaneous tail base injection of 0.1 ml volumes of FCA. Negative control groups received injections of Freund's incomplete adjuvant. DTH paw oedema responses were assessed twenty-four hours after the right hind foot pad challenge with 0.1 mg of MBSA in 0.4 mg of Mycobacterium tuberculosis extract antigen in 0.2 ml volumes of saline on day seven after sensitization. Contralateral paws received control saline injections. The test compounds were orally administered daily on days four, five, six and twice on day seven, one hour before and six hours after antigenic challenge. The results of these tests are given in Table II where the percentage inhibition of oedema formation is given. Doses are given in units of mg/kg p.o.

TABLE II

| Example | Test 1 % inhibition | Test 1 Dose | Test 2 % inhibition | Test 2 Dose | Test 3 % inhibition | Test 3 Dose |
|---|---|---|---|---|---|---|
| 1 | 28 | 50 | 4 | 30 | −19 | 10 |
| 2 | 34 | 50 | −8 | 100 | 22 | 50 |
| 3 | −8 | 50 | 69 | 100 | 48 | 50 |
| 4 | 13 | 50 | 61 | 30 | 61 | 10 |
| 5 | −7 | 50 | 19 | 100 | 52 | 50 |
| 6 | −4 | 10 | 76 | 30 | 47 | 10 |
| 7 | 41 | 50 | 19 | 10 | 33 | 10 |
| 8 | 22 | 50 | 5 | 100 | 51 | 50 |
| 9 | 35 | 50 | 33 | 100 | 70 | 50 |
| 10 | −5 | 10 | 53 | 30 | 79 | 10 |
| 11 | 17 | 50 | 23 | 30 | — | — |

Various modifications of the compounds and methods of the invention may be made without departing from the spirit or scope thereof and it is to be understood that the invention is intended to be limited only as defined in the appended claims.

What is claimed is:

1. A compound selected from the group consisting of a compound of the formula

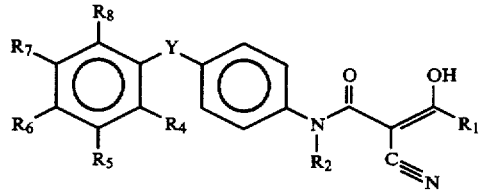

wherein $R_1$ is cycloalkyl of 3 to 6 carbon atoms $R_2$ is hydrogen or alkyl of 1 to 3 carbon atoms, Y is selected from the group consisting of

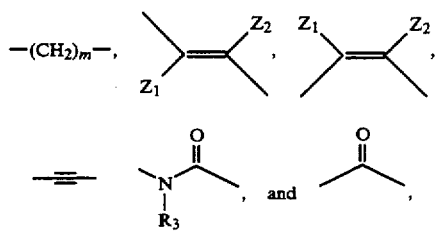

$Z_1$ and $Z_2$ are hydrogen, $R_3$ is methyl, m is an integer from 0 to 2, $R_4$, $R_5$, $R_6$, $R_7$ and $R_8$ are individually selected from the group consisting of hydrogen, halogen, —CN, —NO$_2$, alkyl, alkylthio and alkoxy of 1 to 6 carbon atoms, cycloalkyl of 3 to 6 carbon atoms, —COR$_{10}$, —(CH$_2$)$_n$—CX$_3$, —O—(CH$_2$)$_n$—CX$_3$ and —S—(CH$_2$)$_n$—CX$_3$, R$_{10}$ is selected from the group consisting of hydrogen, alkyl of 1 to 6 carbon atoms and cycloalkyl of 3 to 6 carbon atoms, n is an integer from 0 to 3, X is halogen or $R_6$ and $R_7$ together form —O—CH$_2$—O— and their non-toxic, pharmaceutically acceptable salts with a base.

2. A compound of claim 1 wherein $R_2$ is hydrogen or methyl.

3. A compound of claim 1 wherein $R_1$ is cyclopropyl, $R_2$ is hydrogen or methyl,

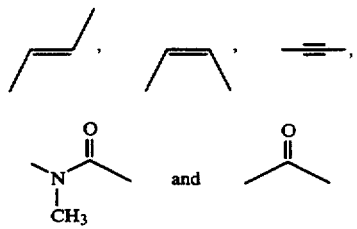

$R_4$, $R_5$, $R_6$, $R_7$ and $R_8$ are individually selected from the group consisting of hydrogen, chlorine, fluorine, bromine, —CN, —NO$_2$, methyl, cyclopropyl, methoxy, methylthio and —COR$_{10}$, —(CH$_2$)$_n$—CF$_3$, —O—(CH$_2$)$_n$—CF$_3$ and —S—(CH$_2$)$_n$—CF$_3$, R$_{10}$ is selected from the group consisting of hydrogen, methyl and cyclopropyl, n is a 0, 1, 2 or 3 or $R_6$ and $R_7$ together form —O—CH$_2$—O—.

4. A compound of claim 1 selected from the group consisting of N-[4-(4'-chlorophenyl-E-ethenyl)-phenyl]-2-cyano-3-cyclopropyl-3hydroxy-prop-2-enamide; N-

[4(4'-fluorophenyl-E-ethenyl)-phenyl]-2-cyano-3-cyclopropyl-3-hydroxy-prop-2-enamide; N-(4-biphenyl-yl-2-cyano-3-cyclopropyl-3-hydroxy-prop-2-enamide; N-[4(4'-fluorophenyl)-phenyl]-2cyano-3-cyclopropyl-3-hydroxy-prop-2-enamide and their salts with a non-toxic, pharmaceutically acceptable base.

5. An anti-inflammatory composition comprising an anti-inflammatory effective amount of a compound of claim 1 and an inert pharmaceutical carrier.

6. A composition of claim 5 wherein $R_2$ is hydrogen or methyl.

7. A composition of claim 5 wherein $R_1$ is cyclopropyl, $R_2$ is hydrogen or methyl,

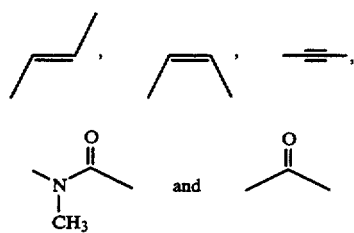

$R_4$, $R_5$, $R_6$, $R_7$ and $R_8$ are individually selected from the group consisting of hydrogen, chlorine, fluorine, bromine, —CN, —$NO_2$, methyl, cyclopropyl, methoxy, methylthio and —$COR_{10}$, —$(CH_2)_n$—$CF_3$, —O—$(CH_2)_n$—$CF_3$ and —S—$(CH_2)_n$—$CF_3$, $R_{10}$ is selected from the group consisting of hydrogen, methyl and cyclopropyl, n is a 0, 1, 2 or 3 or $R_6$ and $R_7$ together form —O—$CH_2$—O—.

8. A composition of claim 5 wherein

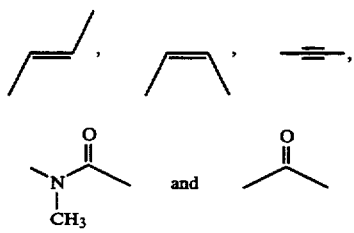

$R_4$, $R_5$, $R_6$, $R_7$ and $R_8$ are individually selected from the group consisting of hydrogen, chlorine, bromine, fluorine, methyl, —$NO_2$ and —$CF_3$.

9. A composition of claim 5 wherein the compound is selected from the group consisting of N-[4-(4'-chlorophenyl-E-ethenyl)-phenyl]-2-cyano-3-cyclopropyl-3-hydroxy-prop-2-enamide; N-[4-(4'-fluorophenyl-E-ethenyl)-phenyl]-2-cyano-3-cyclopropyl-3-hydroxy-prop-2-enamide; N-(4-(4'-fluorophenyl)-phenyl]-2-cyano-3-cyclopropyl-3-hydroxy-prop-2-enamide and their salts with a non-toxic, pharmaceutically acceptable base.

10. A method of treating inflammation in warm-blooded animals comprising administering to warm-blooded animals an anti-inflammatorily effective amount of a compound of claim 1.

11. A method of claim 10 wherein $R_2$ is hydrogen or methyl.

12. A method of claim 10 wherein $R_1$ is cyclopropyl, $R_2$ is hydrogen or methyl,

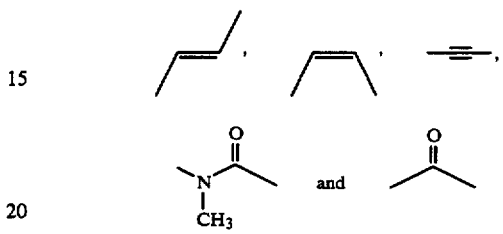

$R_4$, $R_5$, $R_6$, $R_7$ and $R_8$ are individually selected from the group consisting of hydrogen, chlorine, fluorine, bromine, —CN, —$NO_2$, methyl, cyclopropyl, methoxy, methylthio and —$COR_{10}$, —$(CH_2)_n$—$CF_3$, —O—$(CH_2)_n$—$CF_3$ and —S—$(CH_2)_n$—$CF_3$, $R_{10}$ is selected from the group consisting of hydrogen, methyl and cyclopropyl, n is a 0, 1, 2 or 3 or $R_6$ and $R_7$ together form —O—$CH_2$—O—.

13. A method of claim 10 wherein

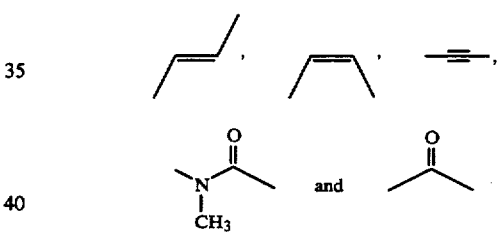

$R_4$, $R_5$, $R_6$, $R_7$ and $R_8$ are individually selected from the group consisting of hydrogen, chlorine, bromine, fluorine, methyl, —$NO_2$ and —$CF_3$.

14. A method of claim 10 wherein the compound is selected from the group consisting of N-[4-(4'-chlorophenyl-E-ethenyl)-phenyl]-2-cyano-3-cyclopropyl-3-hydroxy-prop-2-enamide; N-[4-(4'-fluorophenyl-E-ethenyl)-phenyl]2-cyano-3-cyclopropyl-3-hydroxy-prop-2-enamide; N-[4-biphenyl-yl-2-cyano-3-cyclopropyl-3-hydroxy-prop-2-enamide; N-[4-(4'-fluorophenyl)-phenyl]-2-cyano-3-cyclopropyl-3-hydroxy-prop-2-enamide and their salts with a non-toxic, pharmaceutically acceptable base.

* * * * *